(12) United States Patent
Chaparro Leal et al.

(10) Patent No.: US 11,388,924 B2
(45) Date of Patent: Jul. 19, 2022

(54) NICOTINE ION PAIR FORMULATION NEUTRALIZED WITH CO2 AND PROCESS THEREFOR

(71) Applicant: 10007811 CANADA INC., Montreal (CA)

(72) Inventors: Laura Teresa Chaparro Leal, Montreal (CA); Gérald J. Zagury, Montreal (CA)

(73) Assignee: 10150703 CANADA INC., Calgary (CA)

( * ) Notice: Subject to any disclaimer, the term of this patent is extended or adjusted under 35 U.S.C. 154(b) by 411 days.

(21) Appl. No.: 16/265,594

(22) Filed: Feb. 1, 2019

(65) Prior Publication Data
US 2019/0261672 A1    Aug. 29, 2019

Related U.S. Application Data

(60) Provisional application No. 62/625,467, filed on Feb. 2, 2018.

(51) Int. Cl.
| | | |
|---|---|---|
| *A24B 15/16* | (2020.01) | |
| *A24B 15/32* | (2006.01) | |
| *C07D 401/04* | (2006.01) | |
| *A24B 15/167* | (2020.01) | |

(52) U.S. Cl.
CPC ............ *A24B 15/167* (2016.11); *A24B 15/32* (2013.01); *C07D 401/04* (2013.01)

(58) Field of Classification Search
None
See application file for complete search history.

(56) References Cited

U.S. PATENT DOCUMENTS

2015/0313275 A1* 11/2015 Anderson ............ A61K 31/465
                                                                 131/352

FOREIGN PATENT DOCUMENTS

| KR | 10-1208473 B1 † | 11/2012 |
| KR | 10-1208473 B1 † | 12/2012 |
| WO | 2015/084544 A1 † | 6/2015 |
| WO | 2015084544 A1 † | 6/2015 |

OTHER PUBLICATIONS

10% w/v Nicotine Solution in Propylene glycol, Glycerin, SDS Sheet, Wizard Labs, 2017,3 pages, [online],retrieved from the Internet,[retrieved Apr. 16, 2021, URL:https://wizardlabs.us/image/catalog/msds/SDS_Nicotine_Solution_100mg_Wizard_Labs.pdf>. (Year: 2017).*

Sada, E., et al., "Chemical Kinetics of the Reaction of Carbon Dioxide with Triethanolamine in Non-Aqueous Solvents" The Chemical Engineering Journal, 40 (1989) pp. 7-12.†

Excerpt from Wikipedia on chemistry of bicarbonates, Retrieved Mar. 25, 2021, 1 page https://en.wikipedia.org/wiki/Sodium_bicarbonate.†

\* cited by examiner
† cited by third party

*Primary Examiner* — Dennis R Cordray
(74) *Attorney, Agent, or Firm* — Praxis

(57) ABSTRACT

Nicotine ion pair formulations neutralized with $CO_2$ are disclosed herein. The nicotine ion pair formulations have the general formula $C_{10}H_{14}N_2H^+CO_2Sol^-$, wherein $C_{10}H_{14}N_2$ is nicotine and Sol is a solvent. A process of preparing the nicotine ion pair formulations neutralized with $CO_2$. is also disclosed herein. An e-liquid comprising a nicotine ion pair formulation neutralized with $CO_2$ and the use of the e-liquid in a vaporization device are further disclosed herein. Finally, a vaporization device charged with an e-liquid comprising a nicotine ion pair formulation neutralized with $CO_2$ is disclosed herein.

18 Claims, No Drawings

NICOTINE ION PAIR FORMULATION NEUTRALIZED WITH CO2 AND PROCESS THEREFOR

CROSS REFERENCE TO RELATED APPLICATIONS

This application claims the benefit of U.S. Provisional Application 62/625,467, filed Feb. 2, 2018. The contents of the referenced application are incorporated into the present application by reference.

FIELD

The present disclosure broadly relates to nicotine ion pair formulations. More specifically, but not exclusively, the present disclosure relates to nicotine ion pair formulations neutralized with $CO_2$. Yet more specifically, but not exclusively, the present disclosure relates to nicotine ion pair formulations neutralized with $CO_2$ in the manufacture of e-liquids. Yet more specifically, but not exclusively, the present disclosure relates to devices charged with an e-liquid comprising a nicotine ion pair formulation neutralized with $CO_2$.

BACKGROUND

Nicotine is a tobacco plant alkaloid, addictive to the central nervous system (CNS). Nicotine salts, also known as Nic Salts, are a type of processed nicotine used in electronic liquids (e-liquids) for use in vaporization devices. Many vapers find nicotine salts more satisfying than regular "freebase" nicotine. Freebasing nicotine is a way to increase the potency of nicotine without increasing the dose. To freebase nicotine, cigarette companies add ammonia, usually in the form of diammonium phosphate. The addition of ammonia, a base, deprotonates nicotine, making it cross through membranes in the body much more easily. This makes the drug more "bioavailable" to the lungs, brain and tissues.

Nicotine is a stimulant that releases several neurotransmitters, such as acetylcholine, beta-endorphin, dopamine and serotonin, that may produce physical manifestations such as peripheral vasoconstriction, tachycardia, and elevated blood pressure, and in some cases nausea (PubChem, 2017—Open Chemistry Data Base—https://pubchem.ncbi.nlm.nih.gov/compound/nicotine#section=Top). Nicotine is rapidly absorbed through the respiratory airways reaching the alveoli of the lung. Subsequent to absorption, nicotine crosses the lung/blood interface stream and reaches the brain in an estimated time of 10-20 s. This rapid absorption has been mainly attributed to the significant surface area of the lungs as well as the efficient nicotine dissolution into the lungs fluids at a of about pH 7.4, which facilitates the transfer across membranes. At this pH, approximatively 69% of the nicotine is ionized whereas 31% remains unionized (Benowitz et al., 2009—Nicotine Chemistry, Metabolism, Kinetics and Biomarkers. Handb. Exp. Pharmacol.; (192): 29-60; Lechuga, 2006—WO2006/004646). To that effect, the pH in healthy lungs ranges between 7.38 and 7.42, equivalent to the blood that travels through the body. It is well known that at the lung/blood interface, the "freebase" form is the species that more readily crosses the membrane barrier, resulting in the establishment of an equilibrium between the "freebase" form and the ionized species. Because of their large surface area, the lungs have an inherently significant buffer capacity, such that the aforementioned equilibrium between ionized and unionized nicotine is continuously reestablished. However, studies have shown that nicotine in its ionized (i.e. protonated) form can also cross the lung/blood interface (Nair et al., 1997—Biomembrane Permeation of Nicotine: Mechanistic Studies with Porcine Mucosae and Skin. J Pharm Sci; 86(2): 257-62). Indeed, it was observed that when using pig's nasal mucosa, the permeation of the protonated form was higher than that for the unionized form.

Because nicotine is an agonist of the nicotinic acetylcholine receptor, it can cause side-effects such as irritation, burning sensation, and nausea. It was discovered that by adding diverse types of organic acids to cigarettes and non-smoke tobacco products, these unwanted side-effects could be substantially reduced or even eliminated due to the fact that some of these organic acids can act as antagonists of the acetylcholine receptor or can inhibit the activation of sensory nerve fibers by nicotine (Kobal et al., EP 2 967 125 A2; Lawson et al.—U.S. Pat. No. 4,830.028). Since some of these organic acids are used in the food industry to improve taste, their use with nicotine could thus impart the dual effect of improved taste while also reducing or eliminating the side-effects inherent to tobacco use.

Nicotine is a weak base containing a pair of nitrogen atoms that can be neutralized under the appropriate conditions. To that effect, organic acids having boiling points ranging from 100° C.-250° C. (volatizing under vaping conditions), in ratios ranging from 1:1 to 1:3 (nicotine:acid), are typically used to neutralize nicotine. Moreover, it is imperative that the organic acids display low to no toxicity by inhalation and oral intake (Lawson et al.—U.S. Pat. No. 4,830,028). The acid treatment of nicotine is typically performed at pH values ranging from about 3 to about 8.5 (Cipolla, 2015; Inhaled nicotine replacement therapy. Asian J. of Pharmaceutical Science; 6: 472-480; Lechuga, 2006—WO2006/004646). Above this range, the corresponding nicotine salts typically produce an unpleasant taste and burning throat sensation to the consumer.

SUMMARY

The present disclosure broadly relates to nicotine ion pair formulations. In an aspect, the present disclosure relates to nicotine ion pair formulations neutralized with $CO_2$. In a further aspect, the present disclosure relates to nicotine ion pair formulations neutralized with $CO_2$ in the manufacture of e-liquids. In yet a further aspect, the present disclosure relates to devices charged with an e-liquid comprising a nicotine ion pair formulations neutralized with $CO_2$.

In an aspect, the present disclosure relates to a process of neutralizing nicotine with $CO_2$. In an embodiment of the present disclosure, the process comprises neutralizing nicotine with $CO_2$.

In an aspect, the present disclosure relates to a process of neutralizing nicotine with $CO_2$. In an embodiment of the present disclosure, the process comprises neutralizing nicotine with $CO_2$. In an embodiment of the present disclosure, the nicotine is solvated in a solvent. In an embodiment of the present disclosure, the solvent comprises a polar protic solvent. In yet a further embodiment of the present disclosure, the solvent comprises propylene glycol.

In an aspect, the present disclosure relates to a process of neutralizing nicotine with $CO_2$. In an embodiment of the present disclosure, the process comprises neutralizing nicotine with $CO_2$. In an embodiment of the present disclosure, the process further comprises neutralizing nicotine with an organic acid. In a further embodiment of the present disclosure, the organic acid comprises at least one of a monocarboxylic acid, a dicarboxylic acid, a polycarboxylic acid, an aromatic acid, a nitroaromatic acid, or a combination of any thereof. In yet a further embodiment of the present disclosure, the organic acid comprises glycolic acid.

In an aspect, the present disclosure relates to a nicotine ion pair formulation neutralized with $CO_2$. In an embodiment of the present disclosure, the process comprises neutralizing nicotine with $CO_2$.

In an aspect, the present disclosure relates to a nicotine ion pair formulation neutralized with $CO_2$. In an embodiment of the present disclosure, the process comprises neutralizing nicotine with $CO_2$. In an embodiment of the present disclosure, the nicotine is solvated in a solvent. In an embodiment of the present disclosure, the solvent comprises a polar protic solvent. In yet a further embodiment of the present disclosure, the solvent comprises propylene glycol.

In an aspect, the present disclosure relates to a nicotine ion pair formulation neutralized with $CO_2$. In an embodiment of the present disclosure, the process comprises neutralizing nicotine with $CO_2$. In an embodiment of the present disclosure, the process further comprises neutralizing nicotine with an organic acid. In a further embodiment of the present disclosure, the organic acid comprises at least one of a monocarboxylic acid, a dicarboxylic acid, a polycarboxylic acid, an aromatic acid, a nitroaromatic acid, or a combination of any thereof. In yet a further embodiment of the present disclosure, the organic acid comprises glycolic acid.

In an aspect, the present disclosure relates to a nicotine ion pair formulation neutralized with $CO_2$. In an embodiment of the present disclosure, the nicotine ion pair formulation further comprises an organic acid. In a further embodiment of the present disclosure, the organic acid comprises at least one of a monocarboxylic acid, a dicarboxylic acid, a polycarboxylic acid, an aromatic acid, a nitroaromatic acid, or a combination of any thereof. In yet a further embodiment of the present disclosure, the organic acid comprises glycolic acid.

In an aspect, the present disclosure relates to a nicotine ion pair formulation neutralized with $CO_2$. In an embodiment of the present disclosure, the nicotine ion pair formulation further comprises an organic acid. In a further embodiment of the present disclosure, the organic acid comprises at least one of a monocarboxylic acid, a dicarboxylic acid, a polycarboxylic acid, an aromatic acid, a nitroaromatic acid, or a combination of any thereof. In yet a further embodiment of the present disclosure, the organic acid comprises glycolic acid. In yet a further embodiment of the present disclosure, the nicotine ion pair formulation further comprises a carrier.

In an aspect, the present disclosure relates to a nicotine ion pair formulation neutralized with $CO_2$. In an embodiment of the present disclosure, the nicotine ion pair formulation further comprises an organic acid. In a further embodiment of the present disclosure, the organic acid comprises at least one of a monocarboxylic acid, a dicarboxylic acid, a polycarboxylic acid, an aromatic acid, a nitroaromatic acid, or a combination of any thereof. In yet a further embodiment of the present disclosure, the organic acid comprises glycolic acid. In yet a further embodiment of the present disclosure, the nicotine ion pair formulation further comprises a carrier. In yet a further embodiment of the present disclosure, the nicotine ion pair formulation further comprises a flavoring agent.

In an aspect, the present disclosure relates to a nicotine ion pair formulation of formula $C_{10}H_{14}N_2H^+CO_2Sol^-$, wherein $C_{10}H_{14}N_2$ is nicotine and Sol is a solvent. In an embodiment of the present disclosure, the solvent is a polar protic solvent. In an embodiment, the present disclosure relates to a nicotine ion pair formulation of formula $C_{10}H_{14}N_2H^+CO_2C_3H_7O_2^-$, wherein $C_{10}H_{14}N_2$ is nicotine and $C_3H_7O_2^-$ is propylene glycoxide. In an embodiment of the present disclosure, the nicotine ion pair formulation further comprises an organic acid. In a further embodiment of the present disclosure, the organic acid comprises at least one of a monocarboxylic acid, a dicarboxylic acid, a polycarboxylic acid, an aromatic acid, a nitroaromatic acid, or a combination of any thereof. In yet a further embodiment of the present disclosure, the organic acid comprises glycolic acid resulting in a nicotine ion pair of formula $C_{10}H_{15}N_2^+CO_2C_2H_3O_3^-$.

In an aspect, the present disclosure relates to a nicotine ion pair formulation of formula $C_{10}H_{14}N_2H^+CO_2Sol^-$, wherein $C_{10}H_{14}N_2$ is nicotine and Sol is a solvent. In an embodiment of the present disclosure, the solvent is a polar protic solvent. In an embodiment, the present disclosure relates to a nicotine ion pair formulation of formula $C_{10}H_{14}N_2H^+CO_2C_3H_7O_2^-$, wherein $C_{10}H_{14}N_2$ is nicotine and $C_3H_7O_2^-$ is propylene glycoxide. In an embodiment of the present disclosure, the nicotine ion pair formulation further comprises an organic acid. In a further embodiment of the present disclosure, the organic acid comprises at least one of a monocarboxylic acid, a dicarboxylic acid, a polycarboxylic acid, an aromatic acid, a nitroaromatic acid, or a combination of any thereof. In yet a further embodiment of the present disclosure, the organic acid comprises glycolic acid resulting in a nicotine ion pair of formula $C_{10}H_{15}N_2^+CO_2C_2H_3O_3^-$. In yet a further embodiment of the present disclosure, the nicotine ion pair formulation further comprises a carrier.

In an aspect, the present disclosure relates to a nicotine ion pair formulation of formula $C_{10}H_{14}N_2H^+CO_2Sol^-$, wherein $C_{10}H_{14}N_2$ is nicotine and Sol is a solvent. In an embodiment of the present disclosure, the solvent is a polar protic solvent. In an embodiment, the present disclosure relates to a nicotine ion pair formulation of formula $C_{10}H_{14}N_2H^+CO_2C_3H_7O_2^-$, wherein $C_{10}H_{14}N_2$ is nicotine and $C_3H_7O_2^-$ is propylene glycoxide. In an embodiment of the present disclosure, the nicotine ion pair formulation further comprises an organic acid. In a further embodiment of the present disclosure, the organic acid comprises at least one of a monocarboxylic acid, a dicarboxylic acid, a polycarboxylic acid, an aromatic acid, a nitroaromatic acid, or a combination of any thereof. In yet a further embodiment of the present disclosure, the organic acid comprises glycolic acid resulting in a nicotine ion pair of formula $C_{10}H_{15}N_2^+CO_2C_2H_3O_3^-$. In yet a further embodiment of the present disclosure, the nicotine ion pair formulation further comprises a carrier. In yet a further embodiment of the present disclosure, the nicotine ion pair formulation further comprises a flavoring agent.

In an aspect, the present disclosure relates to an e-liquid comprising a nicotine ion pair formulation neutralized with $CO_2$.

In an aspect, the present disclosure relates to an e-liquid comprising a nicotine ion pair formulation neutralized with $CO_2$. In an embodiment, the present disclosure relates to an e-liquid comprising a nicotine ion pair formulation of formula $C_{10}H_{14}N_2H^+CO_2Sol^-$, wherein $C_{10}H_{14}N_2$ is nicotine and Sol is a solvent. In a further embodiment of the present disclosure, the e-liquid if for use in a vaporization device.

In an aspect, the present disclosure relates to an e-liquid comprising a nicotine ion pair formulation neutralized with $CO_2$. In an embodiment, the present disclosure relates to an e-liquid comprising a nicotine ion pair formulation of formula $C_{10}H_{14}N_2H^+CO_2Sol^-$, wherein $C_{10}H_{14}N_2$ is nicotine and Sol is a solvent. In an embodiment of the present disclosure, the solvent is a polar protic solvent. In an embodiment, the present disclosure relates to a nicotine ion pair formulation of formula $C_{10}H_{14}N_2H^+CO_2C_3H_7O_2^-$, wherein $C_{10}H_{14}N_2$ is nicotine and $C_3H_7O_2^-$ is propylene glycoxide. In a further embodiment of the present disclosure, the e-liquid if for use in a vaporization device.

In an aspect, the present disclosure relates to an e-liquid comprising a nicotine ion pair formulation obtained by a process comprising neutralizing nicotine with $CO_2$.

In an aspect, the present disclosure relates to an e-liquid comprising a nicotine ion pair formulation obtained by a process comprising neutralizing nicotine with $CO_2$. In an embodiment, the present disclosure relates to an e-liquid comprising a nicotine ion pair formulation of formula $C_{10}H_{14}N_2H^+CO_2Sol^-$, wherein $C_{10}H_{14}N_2$ is nicotine and Sol is a solvent. In a further embodiment of the present disclosure, the e-liquid if for use in a vaporization device.

In an aspect, the present disclosure relates to an e-liquid comprising a nicotine ion pair formulation obtained by a process comprising neutralizing nicotine with $CO_2$. In an embodiment, the present disclosure relates to an e-liquid comprising a nicotine ion pair formulation of formula $C_{10}H_{14}N_2H^+CO_2Sol^-$, wherein $C_{10}H_{14}N_2$ is nicotine and Sol is a solvent. In a further embodiment of the present disclosure, the solvent is a polar protic solvent. In a further embodiment, the present disclosure relates to a nicotine ion pair formulation of formula $C_{10}H_{14}N_2H^+CO_2C_3H_7O_2^-$, wherein $C_{10}H_7N_2$ is nicotine and $C_3H_7O_2^-$ is propylene glycoxide. In a further embodiment of the present disclosure, the e-liquid if for use in a vaporization device.

In an aspect, the present disclosure relates to an e-liquid comprising a nicotine ion pair formulation obtained by a process comprising neutralizing nicotine with $CO_2$. In an embodiment of the present disclosure, the process further comprises neutralizing nicotine with an organic acid. In a further embodiment of the present disclosure, the organic acid comprises at least one of a monocarboxylic acid, a dicarboxylic acid, a polycarboxylic acid, an aromatic acid, a nitroaromatic acid, or a combination of any thereof. In yet a further embodiment of the present disclosure, the organic acid comprises glycolic acid. In an embodiment, the present disclosure relates to an e-liquid comprising a nicotine ion pair formulation of formula $C_{10}H_{14}N_2H^+CO_2Sol^-$, wherein $C_{10}H_{14}N_2$ is nicotine and Sol is a solvent. In a further embodiment, the solvent is a polar protic solvent. In a further embodiment, the present disclosure relates to a nicotine ion pair formulation of formula $C_{10}H_{14}N_2H^+CO_2C_3H_7O_2^-$, wherein $C_{10}H_{14}N_2$ is nicotine and $C_3H_7O_2^-$ is propylene glycoxide. In a further embodiment of the present disclosure, the e-liquid if for use in a vaporization device.

In an aspect, the present disclosure relates to a vaporization device comprising an e-liquid as set forth in any of the embodiments of the present disclosure.

In an aspect, the present disclosure relates to a vaporization kit comprising a vaporization device and an e-liquid comprising a nicotine ion pair formulation neutralized with $CO_2$.

In an aspect, the present disclosure relates to a vaporization kit comprising a vaporization device and a container comprising an e-liquid as set forth in any of the embodiments of the present disclosure.

Also disclosed in the context of the present disclosure are embodiments 1 to 48. Embodiment 1 is a nicotine ion pair formulation of formula $C_{10}H_{14}N_2H^+CO_2Sol^-$ wherein $C_{10}H_{14}N_2$ is nicotine and Sol is a solvent. Embodiment 2 is the nicotine ion pair formulation of embodiment 1, having the formula $C_{10}H_{14}N_2H^+CO_2C_3H_7O_2^-$ wherein $C_{10}H_{14}N_2$ is nicotine and $C_3H_7O_2^-$ is propylene glycoxide. Embodiment 3 is the nicotine ion pair formulation according to embodiment 1 or 2, further comprising an organic acid. Embodiment 4 is the nicotine ion pair formulation according to embodiment 3, wherein the organic acid is at least one of a monocarboxylic acid, a dicarboxylic acid, a polycarboxylic acid, an aromatic acid, a nitroaromatic acid, or a combination of any thereof. Embodiment 5 is the nicotine ion pair formulation of embodiment 3 or 4, wherein the organic acid is glycolic acid. Embodiment 6 is the nicotine ion pair formulation according to any one of embodiments 1 to 5, further comprising a carrier. Embodiment 7 is the nicotine ion pair formulation of embodiment 6, wherein the carrier comprises at least one of propylene glycol or vegetable glycerin. Embodiment 8 is the nicotine ion pair formulation according to any one of embodiment 1 to 7, further comprising a flavoring agent.

Embodiment 9 is a process of preparing a nicotine ion pair formulation, the process comprising neutralizing nicotine with $CO_2$. Embodiment 10 is the process according to embodiment 9, further comprising neutralizing the nicotine with an organic acid. Embodiment 11 is the process according to embodiment 10, wherein the organic acid is at least one of a monocarboxylic acid, a dicarboxylic acid, a polycarboxylic acid, an aromatic acid, a nitroaromatic acid, or a combination of any thereof. Embodiment 12 is the process according to embodiment 10 or 11, wherein the organic acid is glycolic acid. Embodiment 13 is the process according to any one of embodiments 9 to 12, wherein the nicotine is solvated in a solvent. Embodiment 14 is the process according to embodiment 13, wherein the solvent comprises a polar protic solvent. Embodiment 15 is the process according to embodiment 14, wherein the solvent comprises propylene glycol.

Embodiment 16 is an e-liquid comprising a nicotine ion pair formulation of formula $C_{10}H_{14}N_2H^+CO_2Sol^-$ wherein $C_{10}H_{14}N_2$ is nicotine and Sol is a solvent. Embodiment 17 is the e-liquid of embodiment 16, wherein the nicotine ion pair formulation has the formula $C_{10}H_{14}N_2H^+CO_2C_3H_7O_2^-$ wherein $C_{10}H_{14}N_2$ is nicotine and $C_3H_7O_2^-$ is propylene glycoxide. Embodiment 18 is the e-liquid of embodiment 16 or 17, wherein the nicotine ion pair formulation further comprises an organic acid. Embodiment 19 is the e-liquid of embodiment 18, wherein the organic acid is at least one of a monocarboxylic acid, a dicarboxylic acid, a polycarboxylic acid, an aromatic acid, a nitroaromatic acid, or a combination of any thereof. Embodiment 20 is the e-liquid of embodiment 18 or 19, wherein the organic acid is glycolic acid. Embodiment 21 is the e-liquid of any one of embodiments 16 to 20, wherein the nicotine ion pair formulation further comprises a carrier. Embodiment 22 is the e-liquid of embodiment 21, wherein the carrier comprises at least one of propylene glycol or vegetable glycerin. Embodiment 23 is the e-liquid of any one of embodiments 16 to 22, wherein the nicotine ion pair formulation further comprises a flavoring agent.

Embodiment 24 is a use of the e-liquid of any one of embodiments 16 to 23 in a vaporization device.

Embodiment 25 is a use of the nicotine ion pair formulation of any one of embodiments 1 to 8 in a vaporization device.

Embodiment 26 is a process of preparing an e-liquid, the process comprising neutralizing nicotine with $CO_2$. Embodiment 27 is the process according to embodiment 26, further comprising neutralizing the nicotine with an organic acid. Embodiment 28 is the process according to embodiment 27, wherein the organic acid is at least one of a monocarboxylic acid, a dicarboxylic acid, a polycarboxylic acid, an aromatic acid, a nitroaromatic acid, or a combination of any thereof. Embodiment 29 is the process according to embodiment 27 or 28, wherein the organic acid is glycolic acid. Embodiment 30 is the process according to any one of embodiments 26 to 29, wherein the nicotine is solvated in a solvent. Embodiment 31 is the process according to embodiment 30, wherein the solvent comprises a polar protic solvent. Embodiment 32 is the process according to embodiment 31, wherein the solvent comprises propylene glycol.

Embodiment 33 is a vaporization device comprising an e-liquid comprising a nicotine ion pair formulation of formula $C_{10}H_{14}N_2H^+CO_2Sol^-$ wherein $C_{10}H_{14}N_2$ is nicotine and Sol is a solvent. Embodiment 34 is the vaporization device of embodiment 33, wherein the nicotine ion pair formulation has the formula $C_{10}H_{14}N_2H^+CO_2C_3H_7O_2^-$ wherein $C_{10}H_{14}N_2$ is nicotine and $C_3H_7O_2^-$ is propylene glycoxide. Embodiment 35 is the vaporization device of embodiment 33 or 34, wherein the nicotine ion pair formulation further comprises an organic acid. Embodiment 36 is the vaporization device of embodiment 35, wherein the organic acid is at least one of a monocarboxylic acid, a dicarboxylic acid, a polycarboxylic acid, an aromatic acid, a nitroaromatic acid, or a combination of any thereof. Embodiment 37 is the vaporization device of embodiment 35 or 36, wherein the organic acid is glycolic acid. Embodiment 38 is the vaporization device of any one of embodiments 33 to 37, wherein the nicotine ion pair formulation further comprises a carrier. Embodiment 39 is the vaporization device of embodiment 38, wherein the carrier comprises at least one of propylene glycol or vegetable glycerin. Embodiment 40 is the vaporization device of any one of embodiments 33 to 39, wherein the nicotine ion pair formulation further comprises a flavoring agent.

Embodiment 41 is a container comprising an e-liquid comprising a nicotine ion pair formulation of formula $C_{10}H_{14}N_2H^+CO_2Sol^-$ wherein $C_{10}H_4N_2$ is nicotine and Sol is a solvent. Embodiment 42 is the container of embodiment 41, wherein the nicotine ion pair. formulation has the formula $C_{10}H_{14}N_2H^+CO_2C_3H_7O_2^-$ wherein $C_{10}H_{14}N_2$ is nicotine and $C_3H_7O_2^-$ is propylene glycoxide. Embodiment 43 is the container of embodiment 41 or 42, wherein the nicotine ion pair formulation further comprises an organic acid. Embodiment 44 is the container of embodiment 43, wherein the organic acid is at least one of a monocarboxylic acid, a dicarboxylic acid, a polycarboxylic acid, an aromatic acid, a nitroaromatic acid, or a combination of any thereof. Embodiment 44 is the container of embodiment 43 or 44, wherein the organic acid is glycolic acid. Embodiment 45 is the container of any one of embodiments 41 to 44, wherein the nicotine ion pair formulation further comprises a carrier. Embodiment 46 is the container of embodiment 45, wherein the carrier comprises at least one of propylene glycol or vegetable glycerin. Embodiment 47 is the container of any one of embodiments 41 to 46, wherein the nicotine ion pair formulation further comprises a flavoring agent.

Embodiment 48 is a vaping kit comprising a vaporization device and a container as defined in any one of embodiments 41 to 47.

The foregoing and other advantages and features of the present disclosure will become more apparent upon reading of the following non-restrictive description of illustrative embodiments thereof, given by way of example only.

DETAILED DESCRIPTION

Glossary

In order to provide a clear and consistent understanding of the terms used in the present disclosure, a number of definitions are provided below. Moreover, unless defined otherwise, all technical and scientific terms as used herein have the same meaning as commonly understood by one of ordinary skill in the art to which this specification pertains.

The word "a" or "an" when used in conjunction with the term "comprising" in the claims and/or the specification may mean "one", but it is also consistent with the meaning of "one or more", "at least one", and "one or more than one" unless the content clearly dictates otherwise. Similarly, the word "another" may mean at least a second or more unless the content clearly dictates otherwise.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the word "consisting" and its derivatives, are intended to be closed ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±1% of the modified term if this deviation would not negate the meaning of the word it modifies.

The term "suitable" as used herein means that the selection of the particular compound or conditions would depend on the specific synthetic manipulation to be performed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 99% of the starting material or substrate is converted to product.

The terms "nicotine ion pair" or "nicotine salt" are used interchangeably herein. Nicotine has a large proton affinity and has been known for decades to yield protonated monomers. A nicotine ion pair may denote a protonated nicotine monomer following, at least partial neutralization with $CO_2$ in a protic solvent. A nicotine salt may denote a protonated nicotine monomer following further treatment of a nicotine ion pair with an organic acid in order to effect further neutralization. It is to be understood that the nicotine salt is also a nicotine ion pair.

In an aspect, the present disclosure broadly relates to nicotine ion pair formulations. In an aspect, the present disclosure relates to nicotine ion pair formulations neutralized with $CO_2$. In a further aspect, the present disclosure relates to nicotine ion pair formulations neutralized with $CO_2$ in the manufacture of e-liquids. In yet a further aspect, the present disclosure relates to devices charged with an e-liquid comprising nicotine ion pair formulations neutralized with $CO_2$.

In an aspect, the present disclosure relates to the neutralization of nicotine using $CO_2$. In an embodiment, present disclosure relates to the neutralization of nicotine using $CO_2$ and an organic acid.

In an aspect, the present disclosure relates to nicotine ion pair formulations neutralized with $CO_2$. In an embodiment of the present disclosure, the nicotine ion pair is further neutralized with an organic acid. In yet a further embodiment, the organic acid is glycolic acid. The nicotine ion pair formulations are suitable for use as e-liquids in vaporization devices and vaping kits.

$CO_2$ is less toxic than most of the organic acids commonly used to produce nicotine salts. Moreover, since $CO_2$ is tasteless it adds no taste to the e-liquid formulations of the present disclosure. Furthermore, the process of neutralizing nicotine with $CO_2$ is less expensive and less time-consuming than the traditional formation of nicotine salts using only organic acids.

In an aspect, the nicotine ion pair formulations of the present disclosure provide for a greater amount of nicotine to be inhaled during vaping but without the harsh taste and other undesirable sensations typically associated with higher nicotine concentrations.

In an embodiment, the present disclosure relates to a process for the preparation of a nicotine ion pair formulation comprising the neutralization of nicotine with $CO_2$ and glycolic acid. The process is based on the principle that a tertiary amine such as nicotine reacts with $CO_2$ in a non-aqueous environment to form an ionic pair.

Various aspects of $CO_2$-amine reactions are discussed in Park et al., 2006—Absorption of carbon dioxide into non-aqueous solutions of N-methyldiethanolamine. Korean J. of Chemistry; 23 (5): 806-811; Lidal, 1992—Carbon dioxide removal in gas treating processes. Theses submitted for the degree of Dr., Eng. University of Trondheim. https://inis.iaea.org/collection/NCLCollectionStore/_Public/26/056/26056565.pdf?r=1&r=1; and Sada, 1989—Chemical kinetics of the reaction of carbon dioxide with triethanolamine in non-aqueous solvents. Chem. Eng. J., 40, 7). Moreover, in previous work related to the use of tertiary amines to neutralize $CO_2$, the use of tertiary alkanolamines in non-aqueous media was proposed for reacting with dissolved $CO_2$ to generate an ion pair in accordance with reaction (I):

$$R_3NH(HSol) + CO_2 \rightarrow R_3NH^+CO_2Sol^- \qquad (I)$$

wherein $R_3NH(HSol)$ represents a solvated alkanolamine with HSol being a non-aqueous solvent. Although nicotine $(C_{10}H_{14}N_2)$ is not an alkanolamine, its reaction with $CO_2$ in a non-aqueous media can nonetheless be illustrated by the above-reaction. Furthermore, it is known that the alcohol group of alkanolamine does not have an important impact on the overall reaction.

The reaction rate of $CO_2$ with an amine in non-aqueous solutions is a pseudo-first order reaction and is represented by the following equation:

$$R_{CO2\text{-}amine(HSol)} = k2[CO_2][amine(HSol)] \qquad (II)$$

The reaction rate of $CO_2$ with nicotine in non-aqueous solutions can be represented by the following equation:

$$R_{CO2\text{-}nicotine(HSol)} = k2[CO_2][nicotine(HSol)] \qquad (III)$$

wherein R represents the rate of reaction between $CO_2$ with nicotine solvated in propylene glycol (PG).

As regarding nicotine and with reference to reaction (I), $R_3NH$ represents nicotine and HSol represents a polar protic solvent. In an embodiment of the present disclosure, the polar protic solvent is propylene glycol. In a further embodiment of the present disclosure, the neutralization of nicotine with $CO_2$ is dependent on the solubility of $CO_2$ in the propylene glycol solvent, which in turn is directly linked to the process pressure and inversely proportional to the process temperature. In yet a further embodiment, the process of neutralizing nicotine with $CO_2$ is carried out at a pH of about 9.5 or less. In yet a further embodiment, the process of neutralizing nicotine with $CO_2$ is carried out at a pH ranging from about 9.5 to about 6.5.

In an aspect of the present disclosure, an organic acid is used to complete the neutralization process. In an embodiment of the present disclosure, the organic acid is at least one of a monocarboxylic acid, a dicarboxylic acid, a polycarboxylic acid, an aromatic acid, a nitroaromatic acid or a combination of any thereof. In yet a further embodiment of the present disclosure, the organic acid comprises glycolic acid. Glycolic acid is a relatively odorless and tasteless α-hydroxy-acid. In an embodiment of the present disclosure, nicotine is contacted with glycolic acid at a ratio of 1:3 (nicotine:glycolic acid).

The nature of the solvent has a direct impact on the reaction between $CO_2$ and amines. Indeed, the number of moles of $CO_2$ that can be dissolved at specific temperatures and pressures is dependent on the nature of the solvent (Gui et al. 2011—Solubility of $CO_2$ in Alcohols, Glycols, Ethers, and Ketones at High Pressures from (288.15 to 318.15° K). Chemical and Engineering Data; 56 (5): 2420-2429). For example, the number moles of $CO_2$ dissolved at 25° C. in ethanol at a pressure of 0.41 MPa is 0.0349; the number moles of $CO_2$ dissolved at 25° C. in propylene glycol at a pressure of 0.38 MPa is 0.0100; and the number moles of $CO_2$ dissolved at 25° C. in acetone at a pressure of 0.52 MPa is 0.0876. It has also been reported that $CO_2$ can be dissolved in water and ethanol (Park et al., 2006—Absorption of carbon dioxide into non-aqueous solutions of N-methyldiethanolamine. Korean J. of Chemistry; 23 (5): 806-8 11; Lidal, 1992—Carbon dioxide removal in gas treating processes. Theses submitted for the degree of Dr., Eng. University of Trondheim. https://inis.iaea.org/collection/NCL-CollectionStore/_Public/26/056/26056565.pdf?r=1&r=1).

In accordance with an embodiment of the present disclosure, nicotine neutralization with $CO_2$ was performed in propylene glycol for e-liquids that are propylene glycol/vegetable glycerin based. During this process, the initial pH for pure nicotine in propylene glycol was above 9.5; following neutralization with $CO_2$, the pH dropped to 7.5. Two further experiments were effected wherein nicotine was neutralized in water (final pH was 6.8) and in vegetable glycerin as the solvent. The neutralization reaction in vegetable glycerin is less favorable in view of the reduced solubility of $CO_2$ (Nunes et al., 2013—Solubility of $CO_2$ in glycerol at high pressures. J. of Fluid Phase Equilibria; 358: 105-107).

It has been reported that at temperatures, in the range of 15-45° C., and at higher pressures, in the range 0.14-4.36 MPa, $CO_2$ becomes more soluble in all tested solvents (Gui et al. 2011—Solubility of $CO_2$ in Alcohols, Glycols, Ethers, and Ketones at High Pressures from (288.15 to 318.15° K). Chemical and Engineering Data; 56 (5): 2420-2429). In an embodiment of the present disclosure, nicotine neutralization with $CO_2$ was performed while maintaining the propylene glycol solvent in an ice bath during neutralization; no significant differences were observed in the resulting nicotine ion pair product. In an embodiment of the present disclosure, the neutralization with $CO_2$ was performed at a temperature ranging from about 0° C. to about 25° C. In a further embodiment, the neutralization with $CO_2$ was performed at temperatures below 0° C. In yet a further embodiment of the present disclosure, the neutralization with $CO_2$ can be performed at a temperature ranging from about −45° C. to about 25° C.

In an embodiment of the present disclosure, the experimental setup described by Bihong, et al., 2015 (Mechanisms of $CO_2$ Capture into Monoethanolamine Solution with Different $CO_2$ Loading during the Absorption/Desorption Processes. J. of Environmental Science technology; 49 (17): 10728-10735) was implemented. Accordingly, a $CO_2$ cylinder was connected to a three-necked round bottomed flask containing nicotine dissolved in propylene glycol. $CO_2$ was continuously supplied to the nicotine and propylene glycol solution at constant pressure and temperature. The second and third necks remained closed with a stopper and samples of nicotine were regularly taken to determine the pH. In a further embodiment of the present disclosure, the pressure was increased to 0.41 MPa, which yielded satisfactory results concerning partial neutralization with $CO_2$ in addition to providing safe working conditions. In a further embodiment of the present disclosure, the neutralization with $CO_2$ was performed at pressures ranging from about 0.1 MPa to about 2.7 MPa.

Nicotine Throat Hit and pH: The Nicotine Throat Hit is the sensation in the throat caused by nicotine as it is inhaled. This sensation ranges from a smooth satisfying catch as the vapor travels down the throat to an intolerable harshness. In an embodiment of the present disclosure, the final pH after neutralization of pure nicotine with $CO_2$ in propylene glycol is about 7.5. Organoleptic tests were conducted on a number of subjects, all subjects agreed that at a pH of 7.5 nicotine at high concentrations (over 18 mg/ml) produces a burning and unpleasant sensation in the throat as well as a feeling of shortness of breath in the chest area. The same subjects agreed that at a pH of under 6.15 (nicotine's pKa at 20° C.; nicotine is fully neutralized), the burning sensation in the throat diminishes or disappears and this was indicated even for nicotine concentrations as high as 40 mg/ml. Moreover, the feeling of shortness of breath also waned or disappeared when decreasing the pH. Of note, the above-described sensations are also somewhat related to the acids used in the formulations with acids such as citric acid, lactic acid and malic acid typically producing an unpleasant feeling.

In an embodiment of the present disclosure, the neutralization of nicotine with $CO_2$ is effected at a temperature of about 25° C. and a pressure of about 0.41 MPa. Under these conditions, the neutralization of nicotine with $CO_2$ can be accomplished at a pH not exceeding 7.5. However, at this pH and at high nicotine concentrations, unpleasant sensations such as a harsh taste as well as shortness of breath are observed. These unpleasant sensations are substantially or completely avoided when adding an organic acid to the nicotine ion pair formulations. The organic acid is typically selected based on volatility under vaping conditions, tastelessness, low toxicity or nontoxicity to human health, ease of manipulation, ability to form liquid salts and propensity to producing an unpleasant sensation such as shortness of breath. In a further embodiment of the present disclosure, the organic acid is glycolic acid. To that effect, nicotine is contacted with glycolic acid at a ratio of 1:3 (nicotine:glycolic acid) forming a liquid salt that is tasteless and that does not result in adverse sensations such as shortness of breath.

In an embodiment of the present disclosure, the final pH after neutralization of pure nicotine with $CO_2$ in propylene glycol is about 6.5.

In an embodiment of the present disclosure, the nicotine ion pair formulation comprises a $CO_2$ concentration of about 0.005 mol/L to about 0.01 mol/L and a nicotine ion pair concentration of about 10 mg/ml to about 40 mg/ml.

In an embodiment of the present disclosure, the nicotine neutralization with $CO_2$ is performed at a temperature ranging from about 0° C. to about 50° C. In a further embodiment of the present disclosure, the nicotine neutralization with $CO_2$ is performed at a temperature ranging from about 2° C. to about 25° C.

In an embodiment of the present disclosure, the nicotine neutralization with $CO_2$ is performed at a pressure ranging from about 0.1 MPa to about 4.4 MPa. In a further embodiment of the present disclosure, the nicotine neutralization with $CO_2$ is performed at a pressure ranging from about 0.2 MPa to about 0.5 MPa.

In an embodiment of the present disclosure, the nicotine ion pair formulation comprises a glycolic acid concentration ranging about 0.8% wt to about 1.8% wt and a nicotine ion pair concentration ranging from about 10 mg/ml to about 40 mg/ml.

In an embodiment of the present disclosure, nicotine neutralization with glycolic acid is performed at a temperature ranging from about 15° C. to about 25° C. In a further embodiment of the present disclosure, nicotine neutralization with glycolic acid is performed at atmospheric pressure.

In an embodiment of the present disclosure, the pH of the nicotine ion pair formulation ranges from about 3 to about 8.5.

In an embodiment of the present disclosure, the nicotine ion pair formulation comprises a suitable carrier. In an embodiment of the present disclosure, the carrier comprises at least one of propylene glycol and vegetable glycerin. In a further embodiment of the present disclosure, the carrier comprises propylene glycol. In a further embodiment of the present disclosure, the carrier comprises vegetable glycerin. In a further embodiment of the present disclosure, the carrier comprises a mixture of propylene glycol and vegetable glycerin. In a further embodiment of the present disclosure, the carrier comprises from about 0% wt to about 100% wt of propylene glycol and from about 100% wt to about 0% wt of vegetable glycerin.

While the present disclosure has been described with reference to specific examples, it is to be understood that the disclosure is not limited to the disclosed examples. To the contrary, the disclosure is intended to cover various modifications and equivalent arrangements included within the spirit and scope of the appended claims.

All publications, patents and patent applications cited in the present disclosure are herein incorporated by reference in their entirety to the same extent as if each individual publication, patent or patent application was specifically and individually indicated to be incorporated by reference in its entirety.

The invention claimed is:

1. A $CO_2$-nicotine ion pair formulation of formula:

$$C_{10}H_{14}N_2H^+CO_2Sol^-$$

wherein $C_{10}H_{14}N_2$ is nicotine and Sol is a polar protic solvent.

2. The $CO_2$-nicotine ion pair formulation of claim 1, having the formula:

$$C_{10}H_{14}N_2H^+CO_2C_3H_7O_2^-$$

wherein $C_{10}H_{14}N_2$ is nicotine and $C_3H_7O_2^-$ is propylene glycoxide.

3. The $CO_2$-nicotine ion pair formulation according to claim 1, further comprising an organic acid.

4. The $CO_2$-nicotine ion pair formulation according to claim 3, wherein the organic acid is at least one of a monocarboxylic acid, a dicarboxylic acid, a polycarboxylic acid, an aromatic acid, a nitroaromatic acid, or a combination of any thereof.

5. The $CO_2$-nicotine ion pair formulation of claim 3, wherein the organic acid is glycolic acid.

6. The $CO_2$-nicotine ion pair formulation according to claim 1, further comprising a carrier.

7. The $CO_2$-nicotine ion pair formulation of claim 6, wherein the carrier comprises at least one of propylene glycol or vegetable glycerin.

8. The $CO_2$-nicotine ion pair formulation according to claim 1, further comprising a flavoring agent.

9. A process of preparing a $CO_2$-nicotine ion pair formulation, the process comprising neutralizing nicotine with $CO_2$, wherein the nicotine is solvated in a polar protic solvent.

10. The process according to claim 9, further comprising neutralizing the nicotine with an organic acid.

11. The process according to claim 10, wherein the organic acid is at least one of a monocarboxylic acid, a dicarboxylic acid, a polycarboxylic acid, an aromatic acid, a nitroaromatic acid, or a combination of any thereof.

12. The process according to claim 10, wherein the organic acid is glycolic acid.

13. The process according to claim 9, wherein the solvent comprises propylene glycol.

14. An e-liquid comprising a $CO_2$-nicotine ion pair formulation of formula:

$$C_{10}H_{14}N_2H^+CO_2Sol^-$$

wherein $C_{10}H_{14}N_2$ is nicotine and Sol is a polar protic solvent.

15. The e-liquid of claim 14, wherein the $CO_2$-nicotine ion pair formulation has the formula:

$$C_{10}H_{14}N_2H^+CO_2C_3H_7O_2^-$$

wherein $C_{10}H_{14}N_2$ is nicotine and $C_3H_7O_2^-$ is propylene glycoxide.

16. The e-liquid of claim 14 wherein the $CO_2$-nicotine ion pair formulation further comprises an organic acid.

17. The e-liquid of claim 16, wherein the organic acid is at least one of a monocarboxylic acid, a dicarboxylic acid, a polycarboxylic acid, an aromatic acid, a nitroaromatic acid, or a combination of any thereof.

18. A vaporization device comprising the e-liquid of claim 14.

* * * * *